United States Patent [19]

Morganson

[11] 3,969,423

[45] July 13, 1976

[54] CONTINUOUS PREPARATION OF 2,4,4,4-TETRACHLOROBUTANOL

[75] Inventor: Neal E. Morganson, Lake Charles, La.

[73] Assignee: Olin Corporation, New Haven, Conn.

[22] Filed: June 25, 1975

[21] Appl. No.: 590,181

Related U.S. Application Data

[63] Continuation-in-part of Ser. No. 372,178, June 21, 1973, abandoned.

[52] U.S. Cl. .................................... 260/633
[51] Int. Cl.² ...................................... C07C 31/34
[58] Field of Search .................................. 260/633

[56] References Cited
UNITED STATES PATENTS 3,399,217   8/1968   Zaslowsky ..................... 260/633
3,399,241   8/1968   Smith ............................. 260/633
3,723,543   3/1977   Kaiser et al. ................... 260/633

FOREIGN PATENTS OR APPLICATIONS 932,741     8/1973   Canada ......................... 260/633
1,207,366  11/1965   Germany ....................... 260/633

Primary Examiner—Howard T. Mars
Attorney, Agent, or Firm—F. A. Iskander; T. P. O'Day

[57] ABSTRACT

A continuous process for preparing 2,4,4,4-tetrachlorobutanol by reacting allyl alcohol with carbon tetrachloride in the presence of a catalyst system comprised of carbon dioxide and an iron-containing material.

11 Claims, No Drawings

CONTINUOUS PREPARATION OF 2,4,4,4-TETRACHLOROBUTANOL

This application is a continuation-in-part of copending U.S. application Ser. No. 372,178, filed June 21, 1973, and now abandoned.

This invention relates to an improved process for making 2,4,4,4-tetrachlorobutanol. More particularly, the invention relates to a novel catalyst system for use in the continuous preparation of 2,4,4,4-tetrachlorobutanol by the reaction of allyl alcohol with carbon tetrachloride.

The compound 2,4,4,4-tetrachlorobutanol, hereinafter referred to as TCBA, is a versatile chemical having a wide range of utility. It reacts in a manner typical of aliphatic alcohols, and its chlorinated nature renders it highly desirable where high chlorine content is needed, for example, as a component of pesticides in agricultural applications and the like. It is also useful as an intermediate in preparing plasticizers for polyvinyl chloride resins. In addition, TCBA may readily be dehydrohalogenated to give 4,4,4-trichlorobutylene oxide. The latter compound is a reactive, high chlorine-containing epoxide which is useful in the preparation of epoxy resins, lubricants, and chlorinated polyether polyols employed in the preparation of polyurethane foam.

It is known to prepare TCBA by the reaction of allyl alcohol with carbon tetrachloride in the presence of a catalyst system comprised of iron powder and/or iron chloride. See for example U.S. Pat. No. 3,399,241 to Smith. It is also known in this art that the inclusion of calcium carbonate in such a catalyst system results in improved yield of TCBA as taught in U.S. Pat. No. 3,399,217 to Zaslowski. However, along with the advantage of improved yield, the use of calcium carbonate has one drawback. This is that the calcium carbonate is a solid which is quite difficult to separate from the TCBA product, and it tends to take on a paste-like consistency thereby plugging up or hindering the flow of materials through the production lines. It does not lend itself to separation by washing and while it can be removed by filtration, special filtration apparatus and techniques must be used for this purpose. Inasmuch as this adds to the cost of making TCBA, its practical effect is to substantially reduce the advantages which obtain by using the calcium carbonate.

Further according to the prior art, it has been taught to catalyze the allyl alcohol-carbon tetrachloride reaction with iron carbonyl. See German Pat. No. 1,207,366. However, along with its relatively high cost, iron carbonyl is a very toxic material. Thus its use on an industrial scale, as contrasted with a closely controlled laboratory scale, presents several handling and safety problems. The cost and practical inconvenience of coping with these problems outweigh any benefit that may derive from using such a catalyst. For this reason, iron carbonyl does not represent a commercially viable alternative for catalyzing the TCBA-forming reaction. Still further, additional problems, which adversely affect product purity and yield, have been encountered in connection with the use of iron carbonyl in the continuous preparation of TCBA.

Now, according to the invention, an improvement has been found in a continuous process for preparing TCBA by the reaction of allyl alcohol with carbon tetrachloride in the presence of an iron-containing catalyst selected from iron, ferric chloride, ferrous chloride and mixtures thereof. The improvement resides in carrying out the reaction in the further presence of carbon dioxide as a supplemental catalyst. Thus pursuant to the invention, the continuous reaction of allyl alcohol with carbon tetrachloride is effected in the presence of a catalyst system comprised of an iron-containing material, as specified above, and carbon dioxide, thereby yielding a TCBA product in high yield.

Except for using the catalyst system described above, the process of the invention can be carried out using prior art techniques. See for example Canadian Pat. No. 932,741 which issued Aug. 28, 1973, the entire disclosure of which is incorporated herein by reference.

More in detail, the continuous preparation of TCBA is carried out by a process which comprises the following continuous steps:

a. feeding into a reactor carbon tetrachloride, allyl alcohol and catalyst, the feed rate being such as to maintain in the reactor an over-all molar ratio, allyl alcohol:carbon tetrachloride, of from about 1:3 to about 1:60, b. under agitated conditions allowing part of the allyl alcohol to react with the carbon tetrachloride, the reaction being carried out at a temperature of about 70°–95°C which permits vapor boil-up, thereby yielding a first liquid phase comprised of TCBA, carbon tetrachloride, allyl alcohol, high boiling by-products and iron chloride and a first vapor phase comprised mainly of carbon tetrachloride, allyl alcohol, water and hydrogen chloride, c. condensing at least a portion of the allyl alcohol and the carbon tetrachloride in the first vapor phase and recycling the recovered portion to the reactor, d. partially evaporating the first liquid phase thereby dividing it into a second liquid phase comprised of TCBA, high boiling by-products, carbon tetrachloride, and iron chloride and a second vapor phase comprised of carbon tetrachloride and allyl alcohol, and e. separating the second liquid phase from the second vapor phase, removing substantially all of the iron chloride, and recovering this second liquid phase as a crude product containing about 75–90% by weight of TCBA.

The reactor used to effect the reaction of allyl alcohol with carbon tetrachloride can be of any suitable or conventional type. Usually, it is provided with a thermometer, an internal stirrer or agitator for mixing the reactants and the catalyst and with heating means such as a jacket for circulating hot water or steam around the reactor. One or more inlets are provided for feeding the reactants and the iron-containing catalyst individually or as a premix.

As noted above, the feed of allyl alcohol and carbon tetrachloride is regulated as to maintain in the reactor a molar ratio, allyl alcohol: carbon tetrachloride, from about 1:3 to about 1:60, and preferably from about 1:10 to about 1:30.

The catalyst system which is used is comprised of an iron-containing material and carbon dioxide. The iron-containing material may be iron, ferric chloride, ferrous chloride or a mixture thereof. Any type of iron may be used such as elemental iron, wrought iron, stainless steel, mixtures thereof and the like. The iron is used in subdivided or powder form, usually comprising particles all of which pass a 40-mesh screen and preferably all of which pass a 150-mesh screen. Particles having a diameter larger than 40-mesh may be employed, but the catalytic effect of these larger particles is reduced inasmuch as their total surface area is smaller.

As indicated earlier, the iron-containing material may be iron powder, ferric chloride, ferrous chloride or a mixture thereof. It is generally preferred, however, to use iron powder, ferrous chloride or a mixture thereof. It should be noted that when using iron powder, it is often necessary to begin the reaction in the added presence of ferric chloride which serves as a reaction initiator. However, once the reaction has been initiated, further additions of ferric chloride are not necessary, although they may still be used if desired.

Pursuant to the process of the invention, along with the iron-containing material the reaction is carried out in the presence of carbon dioxide. Preferably this is supplied to the reactor in the gaseous state and as a separate stream such as by being sparged into the reactive mixture through a separate inlet.

The components of the catalyst system of the invention can be used in any suitable proportion which is sufficient to catalyze the reaction. Thus the exact proportion of each component is not critical; and the term "catalytic proportion," as used in the specification claims herein, is intended to encompass any such proportion. By way of illustration, the iron powder may be used in a proportion from about 0.5 to about 12, and preferably about 1-7, parts per every 100 parts by weight of allyl alcohol reactant. A particularly advantageous range for the iron powder is about 1.5-4.5 parts per 100 parts by weight of the allyl alcohol. As for the ferric chloride and ferrous chloride, illustrative catalytic proportions of each of these materials range from about 1 to about 14, and preferably about 2.5-10, parts per every 100 parts by weight of allyl alcohol. Finally, the carbon dioxide may illustratively be used in a proportion from about 0.001 to about 1.2, and preferably about 0.003-0.6, moles per each mole of allyl alcohol. The most preferred range for the carbon dioxide is about 0.005-0.2 mole per mole of allyl alcohol.

The continuous feeding of reactants and catalyst to the reactor is accompanied by continuous agitation to effect adequate mixing and a high rate of reaction. Furthermore, for optimum results, the continuous reaction of allyl alcohol with carbon tetrachloride is effected at a temperature of about 70°–95°C. A reaction temperature within this range is important for two reasons. One is that it promotes a maximum rate of reaction without otherwise adversely affecting the TCBA product, i.e., this temperature range is not high enough to cause TCBA decomposition. Secondly, by heating the reaction mixture to this temperature, an adequate rate of vapor boil-up, i.e., at least one pound, and more commonly at least about 2 pounds, per every pound of TCBA formed, during the course of the reaction; and in turn this vapor boil-up, inasmuch as it effects removal of most of the water by-product which is formed, results in maximum conversion of the allyl alcohol to TCBA. For it has been found that the presence of water in the system has an adverse effect on the conversion rate. Without intending to be limited to this theory, it is believed that this phenomenon is due to the fact that the presence of water interferes with the catalytic effect of the iron catalyst. In accordance with the preferred embodiments of the invention, a reaction temperature ranging from about 72° to about 90°C is used which brings about a boil-up rate of about 2–10 pounds per every pound of TCBA that is formed.

The continuous reaction of allyl alcohol with carbon tetrachloride may be carried out at any suitable pressure. Thus the reaction pressure is not critical. However, for practical considerations, it is preferable to operate the reaction at ambient pressure conditions.

The retention or residence time inside the reactor may be varied over a wide range such as from about 1 to about 10 hours. In practice, however, a residence time of about 2–6 hours is employed.

As the reaction proceeds at the above indicated temperatures, some of the carbon tetrachloride and allyl alcohol are vaporized along with relatively small proportions of water, hydrogen chloride, chloroform and allyl chloride which are formed as by-products. At least a portion of the vaporized carbon tetrachloride and allyl alcohol is recovered, re-condensed and returned to the reactor. This can be achieved by any suitable or conventional technique as disclosed for example in the above-noted Canadian Pat. No. 932,741. Thus the vapors may be allowed to rise into a fractionating column which may be connected to the upper portion of the reactor. The fractionating column, which can be of conventional type, may in turn be connected to a conventional condenser, which is usually operated at a temperature of about 45°–60°C, and thence to a phase separator where the allyl alcohol-carbon tetrachloride phase is recovered. This is then returned to the reactor via the fractionating column. In this manner, when the vapors initially pass through the fractionating column, some of the allyl alcohol and carbon tetrachloride therein will condense by heat transfer resulting from contact with the liquid passing through the column from the phase separator. Thus by this arrangement partial recovery of the vaporized carbon tetrachloride and allyl alcohol is achieved by condensation within the column, the condensate being directly returned to the reactor; and the condensation and recycling of further portions of the allyl alcohol and carbon tetrachloride vapors is achieved by means of the condenser and phase separator.

The liquid reaction product is withdrawn from the reactor at such a rate as to maintain a residence time within the ranges indicated above. Also it is preferable in practice to so regulate the rates of reactants feed and product withdrawal as to maintain a constant liquid level within the reactor.

The liquid reaction product is comprised mainly of TCBA, carbon tetrachloride, allyl alcohol, high boiling byproducts and iron chloride, i.e., ferric and/or ferrous chloride. This product, after withdrawal from the reactor, is subjected to partial evaporation. This step is carried out, using a conventional evaporator, preferably at a temperature not exceeding about 95°C such as about 60°–92°C, and under partial vacuum, i.e., subatmospheric pressure such as about 20–90 m.m. of mercury. This is in order to prevent TCBA decomposition and further to minimize the evaporation of TCBA while permitting evaporation of substantially all of the allyl alcohol and most of the carbon tetrachloride. Thus typically, the TCBA concentration in the vapor stream flowing out of the evaporator is kept at a level of 2.5% by weight or less.

As a result of the partial evaporation step, the liquid reaction product is divided into a vapor phase and a liquid phase. The vapor phase will be comprised of carbon tetrachloride and allyl alcohol, while the liquid phase will be comprised of over about 70%, and more commonly about 75–90%, by weight of TCBA along with some carbon tetrachloride, high-boiling reaction byproduct, iron chloride and a minor proportion of allyl alcohol. The two phases are then separated, with the vapor phase preferably being thereafter condensed and recyled to the reactor. The liquid phase is finally subjected to conventional purification techniques, such as washing with a dilute aqueous hydrochloric acid solution in order to remove substantially all of the iron chloride therefrom. A crude TCBA product is then recovered which usually contains about 75–93% by weight of TCBA along with high boiling byproducts (usually about 2–24%) and carbon tetrachloride (usually about 1–8%). More commonly this crude product is comprised of 78–90% by weight TCBA along with about 7–20% of high-boiling byproducts and about 1–5% of carbon tetrachloride.

The substantially iron chloride-free crude TCBA product so obtained can be used to advantage as is, and without being subjected to further purification, in the production of 4,4,4-trichlorobutylene oxide which is also referred to as 4,4,4-trichloro-1,2-epoxybutane. Thus it can be reacted with an aqueous solution of a basic dehydrohalogenation agent, e.g., NaOH, whereby it is converted to crude trichlorobutylene oxide; and the latter in turn can be used to advantage as such in the preparation of chlorinated polyether polyols useful in the production of polyurethane foam. See for example U.S. Pat. No. 3,726,855, which issued to M. Lapkin on Apr. 10, 1973.

However, if desired the crude TCBA which is obtained by the process of the invention may be subjected to further purification, such as by distillation or solvent extraction, where a highly purified product is called for.

The process of the invention provides an improved catalytic system for the efficient, continuous production of TCBA in high yields. Along with being made up of readily available materials, this catalytic system provides a highly desirable alternative to prior art catalysts. Thus the process of the invention does away with the need for using calcium carbonate in catalyzing the reaction of allyl alcohol with carbon tetrachloride, thereby obviating the need for costly and burdensome filtration techniques in recovering the TCBA product. In addition, the process of the invention enables the production of TCBA in improved yields as compared with prior art methods utilizing toxic and relatively expensive catalysts such as iron carbonyl. As such it provides a practically viable and economically improved method for the commercial production of TCBA.

The following examples are provided to illustrate the invention. In these examples, all parts and percentages are by weight unless otherwise specified.

EXAMPLE 1

Three separate runs, identified as E-1, C-1 and C-2, were made for the continuous production of TCBA. Except for the catalyst composition used and for minor variations (as described hereafter) connected with the use of each catalyst composition, the three runs were made under similar conditions using a continuous-flow, glass-lined, 100-gallon stirred tank reactor fitted with a packed column and a decanter system for distilling off any water formed during the reaction. Heat was applied to the reactor by continuously circulating hot water at a constant rate and temperature through a jacket surrounding the reactor.

In carrying out each run, carbon tetrachloride, allyl alcohol and catalyst were charged to the reactor on a continuous basis, coupled with the continuous withdrawal of crude TCBA product after an average residence time of about 4–5 hours. So recovered, the product was charged to a rising film evaporator in order to strip off unreacted allyl alcohol and carbon tetrachloride which were recycled to the reactor. The various materials charged to the reactor and their flow rates, including the recycle rate, are described in the Table below. In each run, the flow rates were calibrated such as to maintain a constant level in the reactor, which level was identical for each run. The temperature inside the reactor was also recorded for each run and this is provided in the Table. After removing the unreacted allyl alcohol and carbon tetrachloride from the product, the latter was washed with diluted aqueous hydrochloric acid to remove dissolved iron salts therefrom.

Vapor phase chromatography was used to analyze the product of each run for its content of pure TCBA. The results of this analysis, representing in each case a continuous 24-hour period of operation, are provided in the Table below. The conversion of allyl alcohol to TCBA for each run is also recorded in this Table. This conversion was calculated as a weight percentage, based on the total amount of allyl alcohol charged to the reactor, of allyl alcohol which was converted to TCBA.

Table

|  | E-1 | C-1 | C-2 |
| --- | --- | --- | --- |
| Catalyst Feed |  |  |  |
| Iron powder (lbs./hr.) | 0.40 | 0.86 | 0.80 |
| Calcium carbonate (lbs./hr.) | — | — | 0.58 |
| Carbon dioxide (cu. ft./hr.) | 25.0 |  |  |
| Allyl Alcohol Feed (lbs./hr.) |  |  |  |
| Fresh | 15.1 | 15.1 | 14.1 |
| Recycle | 8.8 | 4.7 | 0.7 |
| Total | 23.9 | 19.8 | 14.8 |
| Carbon Tetrachloride Feed (lbs./hr.) |  |  |  |
| Fresh | 36.3 | 53.5 | 48.2 |
| Recycle | 156.5 | 125.1 | 114.7 |
| Total | 192.8 | 178.6 | 162.9 |
| Average Residence Time | 5.0 | 4.8 | 4.0 |
| Reactor Temperature (°C) | 79.0 | 81.0 | 82.0 |
| Allyl Alcohol Conversion (weight%) | 74.0 | 95.0 | 63.0 |
| Product Assay (VPC, %TCBA) | 85.1 | 74.6 | 82.5 |

As seen from the data provided in the Table, the reactor temperature in Run No. E-1 was lower than that for runs No. C-1 and C-2. This was due to the effect of using carbon dioxide in E-1, the flow rate and temperature of jacket hot water being the same for all three runs. This lower reaction temperature, even though it differs by only a few degrees from the reaction temperatures of the other two runs, is of such effect as to account at least partially for the lower rate of conversion achieved in E-1.

The product of run No. C-1, which was made in the presence of iron powder as the sole catalyst, assayed 74.6% pure TCBA. The product of run No. C-2, which was carried out in the presence of iron powder and calcium carbonate as co-catalysts, was an improvement over that of run No. C-1; however, a preparatory and burdensome step was required here, namely filtration, in order to remove the calcium carbonate catalyst.

By contrast the product of run No. E-1, which was carried out according to the invention, had the dual advantage of a high TCBA concentration (85.1% which exceeds the concentration of the products of both runs C-1 and C-2) and no solids, i.e., no need for any filtration.

EXAMPLE 2

This example was performed using the apparatus and general procedure of Example 1. An allyl alcohol solution in carbon tetrachloride was prepared in which the allyl alcohol concentration was 11.5%. A 1-liter portion of this solution was placed in the reactor along with 2.21 grams of iron powder and 6.01 grams of ferric chloride. Carbon dioxide was fed into this reactor at a constant rate of 3 c.c. per minute. The content of the reactor was heated to, and maintained at, a temperature of 82°C ($\pm$ 1°). After about 6 hours of reaction time, further additions of iron powder and allyl alcohol-carbon tetrachloride solution were begun, accompanied by the simultaneous withdrawal of product from the bottom of the reactor such as to maintain a constant liquid level inside the reactor. The addition of iron powder was maintained at the rate of 0.55 grams every 30 minutes, while the addition of the allyl alcohol-carbon tetrachloride solution was carried out at the rate of 4.167 mls. per minute.

The product continuously withdrawn from the reactor was sampled and analyzed for unreacted allyl alcohol every hour. After several hours of operation, a steady rate of conversion was achieved as indicated by the fact that the content of unreacted allyl alcohol in the withdrawn product became stable with a variance of no more than $\pm$ 0.1%. Thereafter the withdrawn product was stripped of volatiles and periodically analyzed by VPC for its concentration of TCBA. The analysis gave an average TCBA content of 90% (the range was 89–92%).

COMPARISON 3

The identical procedure of Example 2 was followed with one exception. This is that instead of the catalyst system used in that example, a prior art catalyst was used, namely, iron pentacarbonyl. This catalyst was used in a proportion which was calculated to provide the same iron equivalent as used in Example 2. Thus in the initial charge to the reactor, 15.48 grams of iron pentacarbonyl were used; and when further additions of allyl alcohol-carbon tetrachloride solution were commenced they were accompanied by the addition of further iron pentacarbonyl at the rate of 1.94 grams every 30 minutes.

As in the case of Example 2, after several hours of operation, a constant reaction rate was achieved as evidenced by the fact that the allyl alcohol content in the reaction product became stable, varying only to the extent of $\pm$ 0.1%. Thereafter, the product, which was continuously withdrawn at the same rate as used in Example 2, was stripped of volatiles and periodically analyzed for its concentration of TCBA. The analysis gave a TCBA concentration range of 77–82% and an average concentration of 80%. This was well below the concentration level obtained in Example 2.

The results of Example 2 and Comparison 3 demonstrate the improvement which obtains from using the catalyst system of the invention over using iron carbonyl as taught by the prior art.

What is claimed is:

1. In a continuous process for preparing 2,4,4,4-tetrachlorobutanol which comprises reacting allyl alcohol with carbon tetrachloride at a temperature of about 70°–95°C, the improvement of carrying out the reaction in the presence of a catalyst system comprised of catalytic proportions of carbon dioxide and an iron-containing material selected from the group consisting of iron powder, ferrous chloride and a mixture thereof, said catalytic proportion of carbon dioxide being in the range of about 0.001 to about 1.2 moles per each mole of said allyl alcohol, said catalytic proportion of iron powder being in the range of about 0.5 to about 12 parts per every 100 parts by weight of said allyl alcohol, and said catalytic proportion of ferrous chloride being in the range of about 1 to about 14 parts per every 100 parts by weight of said allyl alcohol.

2. The process of claim 1 which comprises the following continuous steps:
   a. feeding into a reactor carbon tetrachloride, allyl alcohol, carbon dioxide and said iron-containing material, using such a feed rate of reactants as to maintain in said reactor an over-all molar ratio, allyl alcohol : carbon tetrachloride, from about 1:3 to about 1:60,
   b. under agitated conditions allowing part of said allyl alcohol to react with said carbon tetrachloride, the reaction being carried out at said temperature of about 70°–95°C which permits vapor boil-up, thereby yielding a first liquid phase comprised of 2,4,4,4-tetrachlorobutanol, carbon tetrachloride, allyl alcohol, high-boiling by-products and iron chloride, and a first vapor phase comprised of carbon tetrachloride, allyl alcohol, water and hydrogen chloride,
   c. condensing at least a portion of said allyl alcohol and said carbon tetrachloride in said first vapor phase, and recycling said portion to said reactor,
   d. partially evaporating said first liquid phase thereby dividing it into a second liquid phase comprised of 2,4,4,4-tetrachlorobutanol, high-boiling by-products, carbon tetrachloride and iron chloride, and a second vapor phase comprised of carbon tetrachloride and allyl alcohol, and
   e. separating said second liquid phase from said second vapor phase, removing substantially all of said iron chloride therefrom, and recovering said second liquid phase as a crude product containing about 75–93% by weight of 2,4,4,4-tetrachlorobutanol.

3. The process of claim 2 wherein the partial evaporation of said first liquid phase is carried out at a temperature not exceeding about 95°C and under partial vacuum.

4. The process of claim 2 wherein when said iron-containing material is iron only, the reaction is initiated in the added presence of ferric chloride, said ferric chloride being added in step (a) to said reactor in a proportion of about 1–14 parts per every 100 parts by weight of said allyl alcohol, the addition being discontinued after the reaction has been initiated.

5. The process of claim 4 wherein said molar ratio, allyl alcohol:carbon tetrachloride, ranges from about 1:10 to about 1:30.

6. The process of claim 5 wherein said carbon dioxide is supplied to said reactor in a gaseous state and at such a rate as to provide about 0.003–0.6 moles per every mole of said allyl alcohol.

7. The process of claim 6 wherein said reaction temperature used in step (b) ranges from about 72° to about 90°C.

8. The process of claim 7 wherein said carbon dioxide is fed to said reactor at such a rate as to provide about 0.005–0.2 moles per every mole of said allyl alcohol.

9. The process of claim 8 which includes the added step of condensing said second vapor phase and recycling it to said reactor.

10. The process of claim 9 wherein said catalyst system consists essentially of carbon dioxide, iron powder, and, as a reaction initiator, ferric chloride, the feed of said ferric chloride being discontinued after the reaction has been initiated.

11. The process of claim 10 wherein said partial evaporation step (d) is carried out at a pressure of about 20–90 m.m. of mercury and a temperature of about 60°–92°C.

* * * * *